United States Patent [19]

Sun

[11] Patent Number: 4,950,766
[45] Date of Patent: Aug. 21, 1990

[54] PREPARATION OF BENZAMIDES USEFUL AS ANTIEMETIC AGENTS

[75] Inventor: Jung-Hui Sun, Dublin, Ohio

[73] Assignee: Erbamont, Inc., Dublin, Ohio

[21] Appl. No.: 411,207

[22] Filed: Sep. 21, 1989

Related U.S. Application Data

[63] Continuation of Ser. No. 115,014, Oct. 29, 1987, abandoned.

[51] Int. Cl.$^5$ ............... C07D 307/79; C07D 405/06; C07C 231/02
[52] U.S. Cl. .................. 548/525; 540/596; 540/610; 546/196; 546/230; 546/233; 548/567; 548/561; 549/355; 549/404; 549/405; 549/462; 549/471; 558/415; 564/86; 564/139

[58] Field of Search .............. 548/525, 561, 567; 549/462, 355, 405; 564/138, 139; 540/596, 610; 546/196, 233; 558/415

[56] References Cited

U.S. PATENT DOCUMENTS 4,888,353  12/1989  Lednicer et al. ............... 514/422

OTHER PUBLICATIONS

Fieser & Fieser, "Reagents for Organic Synthesis"; vol. 1, (1967), pp. 114–116.

*Primary Examiner*—Joseph Paul Brust
*Attorney, Agent, or Firm*—Thompson, Hine and Flory

[57] ABSTRACT

A method for preparing a benzamide by reacting an aromatic acid with an amine having a primary amino group and a secondary amino group wherein the reaction is directed to the primary amino group by first reacting the acid with N,N'-carbonyldiimidazole.

10 Claims, No Drawings

PREPARATION OF BENZAMIDES USEFUL AS ANTIEMETIC AGENTS

This is a continuation of co-pending application Ser. No. 115,014 filed Oct. 29, 1987, now abandoned.

BACKGROUND OF THE INVENTION

The present invention relates to a novel method for preparing benzamides and, more particularly to a method for preparing a class of benzamides (including benzofuran carboxamides) are particularly useful as antiemetic agents for cancer chemotherapy induced emesis because they do not appear to be dopamine antagonists.

U.S. Pat. Nos. 3,177,252 to Thominet and U.S. Pat. 3,342,826 to Miller disclose a number of benzamide derivatives which are useful antiemetic and antipsychotic agents. More recently, European Publication No. 0 147 044 disclosed that benzofuran carboxamides constitute another useful class of antiemetic agents. In addition to exhibiting antiemetic activity, most of these compounds are dopamine antagonists. While the dopaminergic response associated with these compounds can be useful, it can also complicate their administration and limit dosage. This is particularly true when the benzamides are used in high dosages to control the emesis associated with chemotherapy. In this application, the compounds are often accompanied by extrapyramidal side effects.

Recent studies have shown that there is a class of benzamides which are antiemetically effective and which do not exhibit a dopaminergic response. These antiemetics are characterized in that they include a secondary amino group in the amido side chain. A number of these compounds are the subject of related and commonly assigned Application Ser. No. 905,215 filed Sept. 9, 1986, now U.S. Pat. No. 4,772,459, patented 09/20/88. Examples are 5-chloro-N-(2-pyrrolidinylmethyl)-2,3dihydrobenzo-[b]furan-7-carboxamide; 4-amino-5-chloro-N(2-pyrrolidinylmethyl)-2,3-dihydrobenzo[b]furan7-carboxamide and 4-amino-5-chloro-2-methoxy-N(2-pyrrolidinylmethyl)benzamide.

SUMMARY OF THE INVENTION

Benzamides having a secondary amino group in the side chain can be prepared by reacting an aromatic acid with an amine. This amine is characterized in that it includes two amino groups, namely, a primary amino group which is the desired site for the reaction with the acid and formation of the amide and a secondary amino group which preferably does not react with the acid. In order to prepare these benzamides in high yields, syntheses must be designed in which the acid preferentially reacts with the primary amino group. Otherwise, a mixture of products including the reaction product of the primary amino group, the reaction product of the secondary amino group and the bisamide is obtained. Typical synthesis involves protecting the secondary amino group during the reaction with the acid and removal of the protecting group following the reaction. While this synthesis is effective, it would be more advantageous to react the amine directly with the acid without the introduction of the protecting group. Indeed, the introduction of the protecting group and its subsequent removal adds two steps to the overall synthesis.

The present invention provides a method for directly reacting an aromatic acid with an amine having primary and secondary amino groups without the introduction of protecting groups wherein the acid selectively reacts with the primary amino group. The reaction is also advantageous because it is regioselective.

While the principal focus of the present invention is the preparation of benzamides exhibiting antiemetic activity, the teachings herein are useful in any application in which it is desired to selectively react an aromatic carboxylic acid with the primary amino group of an amine also having a secondary amino group.

In accordance with the present invention, an aromatic acid is reacted with N,N'-carbonyldiimidazole to produce an intermediate which is reacted with the amine having primary and secondary amino groups. The objective of this synthesis is to activate the aromatic acid such that it is sufficiently reactive to react with the primary amino group but not sufficiently reactive to react with the secondary amino group in the amine. The acid and the diimidazole are believed to react to form an intermediate amide which exhibits this selective reactivity at reduced temperatures.

Accordingly, one object of the present invention is to provide a method for producing benzamides wherein aromatic acids selectively react with primary amino groups in preference to secondary amino groups.

Another object of the present invention is to provide a method for reacting aromatic acids with 2-aminomethylpyrrolidine and similar amines possessing primary and secondary amino groups without the introduction of protecting groups and wherein the pyrrolidinyl nitrogen does not react with the acid.

These and other objects of the present invention are attained through a process which comprises reacting an aromatic carboxylic acid with N,N'-carbonyldiimidazole and reacting the intermediate with an amine having a primary amino group and a secondary amino group.

In accordance with a preferred embodiment of the invention, the benzamides are the reaction product of an amine of the formulas (IA) and (IB)

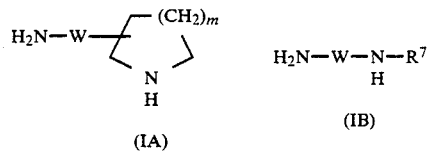

where W is a straight or branched Chain alkylene group containing 1 to 5 carbon atoms and m is 1 to 3 and $R^7$ is an alkyl group having 1 to 4 carbon atoms, a cycloalkyl group having 4 to 8 carbon atoms, an aryl group such as a phenyl group or an aralkyl group such as a benzyl group.

In accordance with a still more preferred embodiment of the invention, the amine is 2-aminomethylpyrrolidine.

Aromatic acids previously reported in the literature as being useful in providing antiemetically active benzamides may be used in the present invention. Useful acids can be represented by the formula (II) or (III)

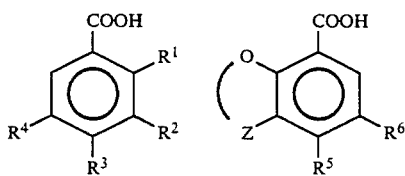

(II)      (III)

wherein in formula (II) R1 is selected from the group consisting of a hydroxyl group, an alkoxy group having 1 to 4 carbon atoms and a hydrogen atom, and R2, R3, and R4 are the same or different and selected from the group consisting of a hydrogen atom, a halogen atom, an alkoxy group, a nitro group, an alkyl group, an alkenyloxy group, an amino group, a monoalkylamino group, a dialkylamino group, a cyano group, a sulfamoyl group, a monoalkylsulfamoyl group, a dialkylsulfamoyl group, a lower acyl group (e.g., having 2 to 4 carbon atoms), a lower acylamido group (e.g., having 2 to 4 carbon atoms), an alkylmercapto group, and a haloalkyl group. In formula (III), Z represents the carbon atoms necessary to complete a 5 to 7-membered ring, and $R^5$ and $R^6$ have the same definition as $R^2$, $R^3$ and $R^4$ in formula (II).

DETAILED DESCRIPTION OF THE INVENTION

The synthesis of the present invention is carried out in two stages. In the first stage, the aromatic acid is reacted with N,N'-carbonyldiimidazole. This reaction can be carried out at room temperature in a dry atmosphere such as argon. The diimidazole is added to a suspension of the carboxylic acid in an inert solvent such as anhydrous tetrahydrofuran (THF) or methylene chloride. The acid and the diimidazole are preferably reacted in stoichiometric amounts or a slight excess of the latter. While the concentration of the reactants can vary, it is preferably about 0.1 to 0.5 mol/l. The reaction is usually complete in about 1 hour. It is believed to produce an intermediate amide having the selective reactivity discussed above according to the following equation.

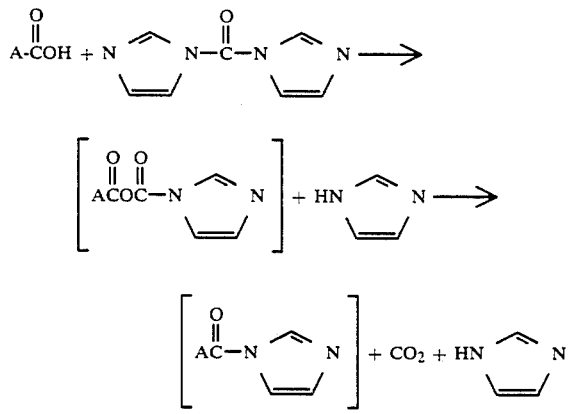

where A is an aromatic moiety.

In the second stage of the reaction, the temperature is lowered and a solution of the amine in a solvent (e.g., THF or methylene dichloride) is added dropwise to the reaction vessel. It is not necessary to recover the reaction product of the first stage. Typically, the reaction is completed within 1 to 3 hours.

While the present invention can be used in the synthesis of benzamides generally when there is a primary and a secondary amino group in the amine to obviate the use of protecting groups, the invention is particularly directed the reaction of amines of the formula (IA).

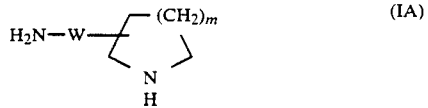

wherein W is a straight chain or branched Chain alkylene group having 1 to 5 carbon atoms and m is 1 to 3. A particularly preferred amine for use in the process of this invention is 2-aminomethylpyrrolidine.

Similarly, aromatic carboxylic acids represented by the formula (II) or (III)

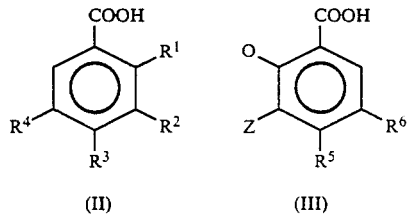

(II)      (III)

are particularly useful in the practice of this invention.

Representative examples of alkoxy groups represented by $R^1$-$R^6$ are alkoxy groups having 1 to 5 carbon atoms such as methoxy, ethoxy and propyloxy.

In formula (III), Z represents the carbon atoms necessary to complete a 5 to 7-membered ring. The invention is particularly useful in reacting compounds in which Z forms a benzo[b]furan or a dihydrobenzo[b]furan ring. Z may be represented by the formula $C_nH_{2n}$ where n is 2 to 4. Useful examples are —CH$_2$CH$_2$—, —CH$_2$CH(CH$_3$)—, —CH$_2$C(CH$_3$)$_2$—, —C(CH$_3$)$_2$CH$_2$—, —CH(CH$_3$)CH$_2$—, —CH$_2$CH(C$_2$H$_5$)—, —CH(C$_2$H$_5$)CH$_2$—, —CH=CH—, —CH=CCH$_3$—, or —CH$_3$C=CH—.

When any of $R^2$-$R^6$ is a halogen atom, the halogen atom may be a fluorine, chlorine or bromine atom. Alkyl and alkenyloxy groups for $R^2$-$R^6$ are typically groups having less than 6 and most preferably 1-3 carbon atoms such as methyl, ethyl, propyl, and propenyloxy. The acyl and acylamido groups are typically aliphatic or aromatic acyl groups having 2 to 7 carbon atoms such as acetamido, formamido, propionamido, benzamido groups.

In order to achieve selective reactivity of the acid intermediate with the primary amino group in the amine, it is necessary to carefully control the reaction temperature. The temperature selected will depend upon the nature of the acid and the amine. To selectively react the primary amino group, a temperature is selected which is sufficiently low that the secondary amino group does not substantially react. Often this will be a function of steric hindrance of the secondary amino group. The more sterically hindered the secondary amino group is, the higher the temperature may be. In reacting acids of formula (III), it has been found that the reaction temperature should not exceed about $-15°$ C. and is preferably in the range of $-30°$ C. to $-20°$ C. If the temperature exceeds about −15° C., the acid tends to react with both the primary and the secondary amino groups. If the temperature is lower than −30° C., the reaction is slow and, in some cases, the acid intermediate may not react.

The invention is illustrated in more detail by the following non-limiting examples.

EXAMPLE 1

Preparation of (S)-5-chloro-N-(2-pyrrolidinylmethyl)-2,3-dihydrobenzo[b]furan-7-carboxamide hydrochloride.

To a suspension of 5-chloro-2,3-dihydrobenzo[b]furan-7-carboxylic acid (20.0 g, 0.1 mol) in 500 ml of methylene chloride was added N,N'-carbonyldiimidazole (16.3 g, 0.1 mol) at room temperature under argon. After stirring for 1 hour, the mixture turned into a clear solution, and the TLC analysis showed disappearance of the starting material. The temperature was lowered to −25° C. with CCl$_4$/dry ice bath and (S)-2-aminomethylpyrrolidine (10.0 g, 0.1 mol) was added dropwise with the temperature maintained at less than −20° C. After 2 hours of stirring at −20° C., the reaction was not complete and an additional 0.1 equivalent (1.0 g) of (S)-2-aminomethylpyrrolidine was added. The reaction was allowed to slowly warm to room temperature overnight. The TLC analysis (Et$_3$N/C-H$_3$OH/CH$_2$Cl$_2$=1:1:8) showed the major spot for the target compound at R$_f$=0.54, a minor spot for bisamide side product at R$_f$=0.94. The solution was washed with 1N NaOH (1×300 ml), and the aqueous layer was extracted with methylene chloride (2×50 ml). The combined organic layers were washed with brine (1×200 ml), and then filtered through a pad of anhydrous MgSO$_4$. To the filtrate was added 5 g of HCl (gas) in 20 ml of methanol and the solution was evaporated to dryness. The crude product (31.5 g, 99.3% yield) was recrystallized from 250 ml of 2-propanol to give 24.5 g (77.2% yield), and a mp 200–201° C.; [α]$_D^{20}$ = +10.2° (C=1.02, CH$_3$OH).

EXAMPLE 2

Preparation of (S)-4-amino-5-chloro-N-(2-pyrrolidinylmethyl)-2,3-dihydrobenzo[b]furan-7-carboxamide hydrochloride.

To a suspension of 4-amino-5-chloro-2,3-dihydrobenzo[b]furan-7-carboxylic acid (71.1 g, 0.33 mol) in 1400 ml of anhydrous THF was added N,N'-carbonyldiimidazole (54 g, 0.33 mol) at room temperature under argon. After 6 hours, an additional 0.02 equivalent (1.08 g) of N,N'-carbonyldiimidazole was added, and the mixture stirred overnight. The TLC analysis showed the disappearance of the starting material. The temperature was lowered to −30° C. with CCl$_4$/dry ice bath and (S)-2-aminomethylpyrrolidine (35 g, 0.35 mol, 1.06 equivalent) in 50 ml of THF was added dropwise over a period of 1 hour while the temperature was maintained at −30° C. After stirring at −20° C. to −30° C. for another 2 hours, the reaction was completed. The solvent in the reaction mixture was evaporated and the remaining dark brown oil was diluted with 1000 ml of methylene chloride. The organic solution was washed with 1N NaOH (350 ml, 150 ml), brine (150 ml), and filtered through a pad of anhydrous MgSO$_4$. To the organic filtrate was added 24 g of HCl (gas) in 100 ml of 2-propanol with stirring and then sonicated overnight. The resulting precipitates were collected on a filter, washed with methylene chloride to give 79.8 g of the hydrochloride of the target compound (72.8% yield) as a white solid. A total of 140 g of the hydrochloride was recrystallized by first dissolving in 300 ml of H$_2$O and then adding 900 ml of 2-propanol to yield 102 g of pure product after drying at 60–70° C. (water bath) under pump vacuum overnight, mp 232.5–233.5° C. (dec);[β]$_D^{20}$= +9.6° (C=1.0; MeOH).

EXAMPLE 3

Preparation of (R)-5-chloro-N-(2-pyrrolidinylmethyl)-2,3-dihydrobenzo[b]furan-7-carboxamide hydrochloride.

To a suspension of 5-chloro-2,3-dihydrobenzo[b]furan-7-carboxylic acid (1.97 g, 10 mmol) in 50 ml of methylene chloride was added N,N'-carbonyldiimidazole (1.62 g, 10 mmol) at room temperature under argon. After stirring for 5 hr, the mixture turned into a clear solution. The solution was cooled with CCl$_4$/dry ice bath and (R)-2-aminomethylpyrrolidine (1.1 g, 11 mmol) in 5 ml of methylene chloride was added dropwise while the reaction temperature was maintained at −15° C. The reaction was completed within 1 hr. The solution was washed with 2N NaOH (1×50 ml) and brine (1×50 ml), dried over anhydrous MgSO$_4$, filtered and the solvent in the filtrate evaporated to give 1.5 g of the product as its free base. This was converted to its HCl salt and recrystallized from 2-propanol to yield 0.87 g of a white solid, mp 198–200° C.; [β]$_D^{20}$= −10.6° (C=0.5; CH$_3$OH).

EXAMPLE 4

Preparation of (R)-4-amino-5-chloro-N-12-pyrrolidinylmethyl)-2,3-dihydrobenzo[b]furan-7-carboxamide hydrochloride.

To a suspension of 4-amino-5-chloro-2,3-dihydrobenzo[b]furan-7-carboxylic acid (4.27 g; 20 mmol) in 100 ml of anhydrous THF was added N,N'-carbonyldiimidazole at room temperature under argon. After 2 hours, an additional 0.1 g of N,N'-carbonyldiimidazole was added, and the mixture stirred overnight. The temperature was lowered to −25° C. with CCl$_4$/dry ice and (R)-2-aminomethylpyrrolidine (2.2 g; 20 mmol) in 10 ml of THF was added dropwise. The mixture was then allowed to warm slowly to room temperature overnight. The solvent in the reaction mixture was evaporated and the remaining material was diluted with methylene chloride. The organic solution was washed with 1N NaOH (2×50 ml), brine (1 ×50 ml), filtered through a pad of anhydrous MgSO$_4$ and evaporated to give 4.03 g (60.7% yield) of the free base as a white solid. 3.5 g of this free base was converted to its hydrochloride salt and recrystallized successively from 2-propanol and water/2-propanol to yield 1.75 g of analytically pure product as a white powder; mp 228.5° C.; [β]$_D^{20}$= −9.2° (C=0.5; CH$_3$OH).

EXAMPLE 5

Preparation of (S)-4-Amino-5-chloro-2-methoxy-N-(2-pyrrolidinylmethyl)benzamide dihydrochloride.

To a suspension of 4-amino-5-chloro-2-methoxybenzoic acid (6.05 g; 30 mmol) in 150 ml of anhydrous THF was added N,N'-carbonyldiimidazole (4.86 g; 30 mmol) at room temperature under argon. After 4 hours, additional 0.58 g of N,N'-carbonyldiimidazole was added. The temperature was lowered to −30° C. and (S)-2- aminomethylpyrrolidine (5.4 g; 54 mmol) in 15 ml of THF was added dropwise. The mixture was allowed to warm slowly to room temperature overnight. The solvent in the reaction mixture was evaporated and the remaining material was diluted with methylene chloride. The organic layer was washed with 1N NaOH, filtered through a pad of anhydrous MgSO$_4$ and evaporated to give 6.88 g (78%) of the free base. To this in 50 ml of methanol with ice-bath cooling was added 3.4 g of HCl (g) in 10 ml of methanol. After stirring for a few hours, the solvent was evaporated. The residue was recrystallized from 2-propanol to yield 5.59 g of a pale cream solid, mp 200–203.5° C.; $[\beta]_D^{20} = +11.1°$ (C=1.0; CH$_3$OH).

EXAMPLE 6

Preparation of 5-chloro-N-(2-ethylaminoethyl)-2,3-dihydrobenzo[b]furan-7-carboxamide hydrochloride.

To a suspension of 5-chloro-2,3-dihydrobenzo[b]furan-7-carboxylic acid (2.0 g; 10.1 mmol) in 50 ml of anhydrous THF was added N,N'-carbonyldiimidazole (1.68 g; 10.4 mmol) at room temperature under argon. After 45 minutes, the resulting clear solution was cooled with dry ice/acetone bath and N-ethylethylenediamine (0.93 g; 10.4 mmol) in 5 ml of THF was added dropwise. The solution was allowed to slowly warm to room temperature overnight. A small amount of precipitates formed in the solution was filtered off, and the solvent in the filtrate was evaporated. The residue was diluted with methylene chloride, washed with 1N NaOH (1×40 ml), brine (1 ×40 ml), dried over anhydrous MgSO$_4$, and evaporated to give 1.95 g (72.6% yield) of a light yellow viscous liquid. To this in 20 ml of methanol was added 0.8 g of HCl (g) in methanol. After 2 hours of stirring, the solvent was evaporated; and the resulting residue was recrystallized from 2-propanol to give 1.55 g of a white solid, mp 247–248.5° C.

Having described the invention in detail and by reference to specific embodiments thereof, it will be apparent that numerous modifications and variations are possible without departing from the spirit and scope of the invention as defined by the following claims:

What is claimed is:

1. A method for the preparation of a benzamide which comprises reacting a benzoic acid represented by the formula (II) or (III)

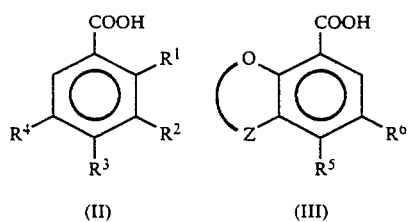

wherein $R^1$ is an alkoxy group having 1 to 4 carbon atoms, a hydroxyl group or a hydrogen atom, $R^2$, $R^3$, $R^4$, $R^5$ and $R^6$ are the same or different and selected from the group consisting of a hydrogen atom, a halogen atom, an alkoxy group, a nitro group, an alkyl group, an alkenyloxy group an amino group, a monoalkylamino group, a dialkylamino group, a cyano group, a sulfamoyl group, a monoalkylsulfamoyl group, a dialkylsulfamoyl group, a lower acyl group, a lower acylamido group; an alkylmercapto group, and a halomethyl group; and Z represents the carbon atoms necessary to complete a 5 to 7-membered ring, and $R^5$ and $R^6$ have the same definition as $R^2$, $R^3$ and $R^4$ in formula (II) with N,N'-carbonyldiimidazole in an inert solvent to produce an intermediate, and reacting said intermediate with a solution of an amine having a primary and a secondary amino group of the formula (IA) or (IB)

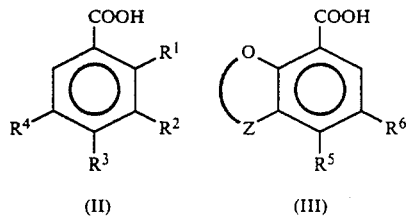

where W is a straight or branched chain alkylene group having 1 to 5 carbon atoms and m is 1 to 3, $R^7$ is selected from the group consisting of an alkyl group having 1 to 4 carbon atoms, a cycloalkyl group having 4 to 8 carbon atoms, a phenyl group and a benzyl group; wherein said amine is reacted in an equimolar or greater amount and said reaction is carried out at a temperature such that said intermediate selectively reacts with said primary amino group and does not substantially react with said secondary amino group.

2. The method of claim 1 wherein said amine is (S)-2-aminomethylpyrrolidine, (R)-2-aminomethylpyrrolidine or racemic 2-aminomethylpyrrolidine.

3. The method of claim 2 wherein said temperature is less than −15° C.

4. The method of claim 1 wherein said acid is represented by the formula (II).

5. The method of claim 1 wherein said acid is represented by the formula (III).

6. The method of claim 4 wherein said acid is 4-amino-5-chloro-2-methoxybenzoic acid.

7. The method of claim 6 wherein said amine is (S)-2-aminomethylpyrrolidine.

8. The method of claim 5 wherein said acid is 5-chloro-2,3-dihydrobenzo[b]furan-7-carboxylic acid or 4-amino-5-chloro-2,3-dihydrobenzo[b]furan-7-carboxylic acid.

9. The method of claim 8 wherein said amine is (S)-2-aminomethylpyrrolidine.

10. The method of claim 3 wherein said temperature is in the range of approximately −30° C. to −20° C.

* * * * *

UNITED STATES PATENT AND TRADEMARK OFFICE
CERTIFICATE OF CORRECTION

PATENT NO. : 4,950,766
DATED : August 21, 1990
INVENTOR(S) : Jung-Hui Sun

It is certified that error appears in the above-identified patent and that said Letters Patent is hereby corrected as shown below:

Column 8, lines 19-28, delete formulas (II) and (III) and insert the following formulas (IA) and (IB):

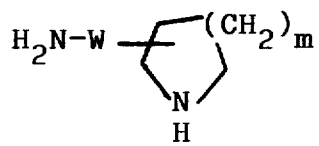 (IA)  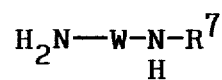 (IB)

Signed and Sealed this

Fifteenth Day of September, 1992

*Attest:*

DOUGLAS B. COMER

*Attesting Officer*  *Acting Commissioner of Patents and Trademarks*